United States Patent [19]

Horodysky

[11] 4,175,043

[45] Nov. 20, 1979

[54] METAL SALTS OF SULFURIZED OLEFIN ADDUCTS OF PHOSPHORODITHIOIC ACIDS AND ORGANIC COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 944,448

[22] Filed: Sep. 21, 1978

[51] Int. Cl.² .................. C10M 1/48; C10M 3/42; C07G 17/00
[52] U.S. Cl. ..................... 252/32.7 E; 252/400 A; 260/125
[58] Field of Search ............. 252/32.7 E, 400 A; 260/125

[56] References Cited

U.S. PATENT DOCUMENTS

| | | | |
|---|---|---|---|
| 2,993,856 | 7/1961 | Heisig et al. | 252/32.7 E |
| 3,471,404 | 10/1969 | Myers | 252/45 |
| 3,646,172 | 2/1972 | Myers | 260/928 |

*Primary Examiner*—Irving Vaughn
*Attorney, Agent, or Firm*—Charles A. Huggett; Raymond W. Barclay; Claude E. Setliff

[57] ABSTRACT

A novel product formed by forming the metal salt of the product of reaction between a dialkyl or diaryl phosphorodithioic acid and a sulfurized olefin possesses among other things, good antiwear and antioxidant activity. Organic compositions containing a minor amount thereof also possess good lubricating characteristics.

24 Claims, No Drawings

METAL SALTS OF SULFURIZED OLEFIN ADDUCTS OF PHOSPHORODITHIOIC ACIDS AND ORGANIC COMPOSITIONS CONTAINING SAME

BACKGROUND OF THE INVENTION

1. Field of the Invention

This invention is directed to novel compounds comprising metal salts of adducts of alkyl or aryl phosphorodithioic acids and a sulfurized olefin.

2. Summary of the Prior Art

Sulfurized olefins are known to be effective extreme pressure agents or load carrying additives for lubricating oils. See U.S. Pat. Nos. 3,703,504; 3,697,499 and 3,471,404.

Phosphorodithioic acids have been reacted with olefins, as disclosed, for example, in U.S. Pat. Nos. 3,646,172 and 3,350,348, and A. A. Oswald, Journal Organic Chemistry, 27, 2439 (1962). However, none of these processes are similar to the instant process nor are the compounds so produced similar to the novel adducts of this invention.

It has now been discovered that when a dialkyl or diaryl phosphorodithioic acid is added in low concentration to the unsaturated components of certain sulfurized olefins and then treated with a reactive metal salt, low phosphorus (0.1-10%), high sulfur (ca. 20% or more), low ash content products result. These products have improved oil solubility, odor, and copper strip corrosivity characteristics as compared to the sulfurized olefin and impart several desirable characteristics to organic substrates, e.g., lubricating oils, when incorporated therein.

SUMMARY OF THE INVENTION

This invention is directed to organothiophosphorus compounds comprising the metal salt or complex of the reaction product of (1) a phosphorodithioic acid having the general formula

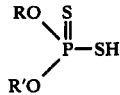

wherein R and R' are hydrocarbyl and are the same or different with each having up to about 30 carbon atoms and (2) a sulfurized olefin. R and R' may each be alkyl of 1 to about 30 carbon atoms, aryl and alkaryl or aralkyl of 7 to about 30 carbon atoms. Accordingly, R and R' may be selected from a group consisting of methyl, ethyl, n-propyl, isopropyl, n-butyl, isobutyl, pentyl or amyl, hexyl, ethylhexyl, oleyl, octadecyl, eicosyl, triacontyl, oleyl, phenyl, alkyl phenyl, phenylalkyl and the like, and mixtures thereof.

The sulfurized olefin contains reactive olefinic sites and may be derived from a process comprising sulfohalogenating a hydrocarbon olefin having a single double bond and having from 2 to about 8 carbon atoms per molecule with a sulfur halide selected from the group consisting of sulfur chlorides and sulfur bromides to form a sulfohalogenated intermediate and thereafter sulfurizing and dehalogenating said intermediate by treatment with an aqueous alkali metal monosulfide solution such as described in U.S. Pat. No. 3,703,504, but this class of reactant is not limited thereto. The alkali metal monosulfide solution may comprise sodium, potassium, or lithium sulfide and may contain sodium hydroxide, sodium hydrosulfide, sodium cresylates, sodium sulfate, sodium chloride, oil and ferrous sulfide. The sulfurized olefins made by variations of the process or by other process known to the art which contain reactive olefinic sites and have a sulfur content of about 20% and above may be employed in the invention. Dimethalkyl sulfides such as

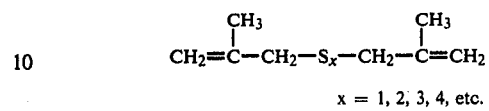

x = 1, 2, 3, 4, etc.

which can be formed by the reaction of methallyl chloride with an alkali metal monosulfide, alkali metal disulfide or alkali metal polysulfide may be employed in this invention. The metal of the metal salt may be selected from Groups IB, IIA, IIB, IVA, VIB and VIII of the Periodic Table.

This invention is also directed to organic compositions comprising a major amount of an organic medium normally subject to deterioration and a minor amount of an additive sufficient to impart antiwear, antioxidant, detergent, extreme pressure and antirust characteristics thereto comprising an organothiophosphorus compound in accordance with this invention and wherein said organic medium is a lubricant from among oils of lubricant viscosity, hydrocracked oils, minerals oils or fractions thereof, synthetic oils or mixtures of synthetic and mineral oils, automotive oils, gear oils and transmission fluids, hydraulic oils, waxes and greases prepared from said oils of lubricating viscosity.

DESCRIPTION OF SPECIFIC EMBODIMENTS

The phosphorodithioic acids in accordance with this invention are generally prepared from the reaction of a suitable phosphorus sulfide, e.g., phosphorus pentasulfide with a variety of phenolic or alcoholic materials, preferably a hydroxylic compound ROH where R may be aryl or alkyl of up to about 30 carbon atoms. A non-exhaustive list of suitable hydroxylic compounds include phenol, methanol, ethanol, n-propanol, i-propanol, n-butanol, i-butanol, primary and secondary pentanols, hexanol, ethylhexanol, oleyl alcohol, eicosyl alcohol, triacontyl alcohol and mixtures thereof.

The preparation of the phosphorodithioic acids may be carried out in any convenient manner known to the art. These acids may also be obtained commercially or made, for example, by slowly reacting a mixture of phosphorus sulfide and the aforementioned hydroxylic component.

Sulfurized olefins useful herein are generally described in U.S. Pat. No. 3,703,504 the entirety of which is incorporated herein by reference. This class of reactant, however, is not limited thereto.

Generally speaking, the sulfurized olefins may be obtained via a process which comprises sulfohalogenating an olefin with a sulfur halide in the presence of a catalytic quantity (i.e., 0.2-10 wt. % based on the halide) of a lower aliphatic alcohol (such as methanol, ethanol, propanol, i-propanol, butanol, i-butanol, i.e., having up to about 10 carbon atoms) to form a sulfohalogenated organic intermediate, and thereafter sulfurizing and dehalogenating said intermediate in the presence of a substantial quantity of lower aliphatic alcohol, e.g., from 10 to about 50% by weight of the adduct by treatment with an aqueous alkali metal sulfide solution, or an aqueous alkali metal monosulfide solution (which can be derived, for example, from a spent aqueous alkali metal hydroxide effluent from hydrocarbon purification) having a substantial combined sulfur content thus producing an organic sulfide of high combined sulfur content.

A wide variety of olefinic substances may be charged to the initial sulfochlorination reaction including olefins having a single double bond as terminal or internal double bonds. The olefinic substances usually contain from about 2 to 8 or more carbon atoms per molecule in either straight, branched chain or cyclic compounds. These may be exemplified by ethylene, propylene, butene-1, cis- and trans- butene-2, isobutylene, diisobutylene, triisobutylene, the pentenes, cyclopentene, the hexenes, cyclohexene, the octenes and decene-1. Isobutylene is generally the preferred olefinic reactant. In general, $C_{3-6}$ olefins or mixtures thereof are desirable for preparing sulfurized products for use herein as lube oil additives; the combined sulfur content of the product decreases with increasing carbon content while its miscibility with oil is lower for propylene and ethylene derivatives.

The other reactant in the first stage is preferably sulfur monochloride ($S_2Cl_2$); but other similar compounds such as sulfur dichloride and $S_3Cl_2$ and the corresponding sulfur bromides as well as the dimethylalkylsulfides and dimethylalkylpolysulfides, may be employed in an amount which will provide a quantity of sulfur corresponding to desirable reactant ratios for sulfur monochloride. The molar ratio of olefin to sulfur monohalide may range from about 1:1 up to 1.7:1 or more. In the case of isobutylene and sulfur monochloride, the optimum ratio appears to be between about 1.55:1 and 1.60:1.

The initial reaction can be catalyzed with a lower aliphatic alcohol containing from 1 to 4 carbon atoms, as exemplified by methanol, ethanol, propanol and isopropanol. Of these, methanol and ethanol are usually preferred. The spent aqueous alkali metal hydroxide effluent as mentioned hereinabove is derived primarily from spent organic caustic liquors issuing from integrated refinery processes.

The sulfurized olefins produced by the above-described process have a very high sulfur content of from about 20% by weight to about 55% by weight (typically about 46-48% combined sulfur) and are substantially devoid of free sulfur. Other sulfurized olefins made by variations of this process or by other processes known to the art which contain reactive olefinic sites and have a sulfur content of about 20% and above may also be employed in this invention. The novel compounds of this invention may thus be prepared by adding phosphorodithioic acids in low concentrations to such sulfurized olefins. These compounds have a low phosphorus content, i.e. from about 0.1 to about 10 weight percent, and a high sulfur content of about 20 to about 50% by weight. The low phosphorus content inter alia may account for improved oil solubility, improved odor and improved copper strip corrosivity.

The reaction is usually carried out at temperatures of from about 75° to 120° C., preferably from 80°-110° C., under atmospheric pressure (although higher pressures may be used if desired) for periods of up to about 16-20 hours, e.g., preferably from about 1 to about 10 hours or more. The reaction mixture is heated with agitation to the desired temperature. The reaction may be accelerated by sparging catalytic amounts of hydrogen sulfide to the reaction vessel to increase the product yield. The reaction may also be carried out in the absence of any added solvent or it may be carried out in a non-reactive solvent such as pentane, hexane, heptane, cyclohexane, benzene, toluene and the like or a refined petroleum oil may be employed therefor.

The metal salts usable are those containing metals from Groups IB, IIA, IIB, IVA, VIB, and VIII of the Periodic Table. The preferred metals are magnesium, zinc, cadmium, barium, cobalt, calcium, nickel, copper, molybdenum, lead and tin. The anion, which can be selected from among the oxides, hydroxides, carbonates, sulfates, nitrates, acetates and citrates is not critical.

The reaction is carried out at temperatures of from about 30° C. to about 130° C., preferably about 70° C. to about 100° C. for from about 1 to about 10 hours, or preferably from about 2 to about 4 hours. Desirable solvents which can be used include hydrocarbon solvents such as hexane, benzene, toluene, etc. or alcoholic solvents such as methanol, ethanol, propanol, isopropanol, butanol, etc. The preferred solvent is isopropanol.

The novel compounds comprising a salt of an adduct of dialkyl or diaryl phosphorodithioic acid as heretofore described with sulfurized olefins (such as those sulfurized olefins disclosed in U.S. Pat. No. 3,703,504) may be used effectively to impart to organic media, particularly to lubricating oils and greases, the properties mentioned hereinabove. An effective amount of the additive compound for all of the properties mentioned above will range from about 0.01% to about 10% by weight. Preferably the organic medium or substrate, e.g., oil of lubricating viscosity contains from about 0.1 to 5% and more preferably from about 0.5 to about 2% by weight of the total weight of the lubricant composition. As hereinbefore indicated, the organic sulfur- and phosphorus-containing complexes may be incorporated into any lubricating media which can include oils of lubricating viscosity and also greases in which any of the aforementioned oils are employed as vehicles. In general, synthetic oils can also be effectively protected against the above-noted deterioration or degradation. They may also be employed in combination with mineral oils, and ester base stock, or as grease vehicles. Typical synthetic vehicles include polyisobutylene, polybutenes, hydrogenated polydecenes, polypropylene glycol, polyethylene glycol, trimethylolpropane esters, neopentyl alcohol and pentaerythritol esters, di(2-ethylhexyl) sebacate, di(2-ethylhexyl) adipate, dibutyl phthalate, fluorocarbons, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxyphenyl) ether and phenoxyphenyl ether.

The following Examples 1 through 16 illustrate the preparation of the metal salt-treated phosphorodithioic acid-sulfurized olefin adduct.

EXAMPLE 1

Preparation of Sulfurized Olefin

Sulfurized olefin was prepared in accordance with Example 1 of U.S. Pat. No. 3,703,504 using isobutylene. The yield of sulfurized organic product amounted to 98% of theory, has a sulfur content of 47% by weight and a chlorine content of only 0.11% as well as a clear, light orange brown color, and a high flash point of 250° F.

EXAMPLE 2

Preparation of Sulfurized Olefin

Sulfurized olefin was prepared in general accordance with Example 6 of U.S. Pat. No. 3,703,504. A mixture of butylenes was sulfurized using the same reaction conditions described and an equivalent molar ratio of flake sodium monosulfide ($Na_2S$). The olefin mixture employed in this instance had the following composition by volume:

| Component | Volume Percent |
| --- | --- |
| Isobutylene | 90.5 |
| Trans-2-butane | 5.9 |
| Cis-2-butene | 2.6 |
| Butadiene | 1.0 |
| | 100.0 |

The product had the following characteristics:
Sulfur content, Wt. %—45.87%
Chlorine content, Wt. %—0.27%
Viscosity—12.1 cs/210° F.

EXAMPLE 3

Adduct of O,O-Diisobutylphosphorodithioic Acid

O,O-Diisobutylphosphorodithioic acid was made by the reaction of $P_2S_5$ with isobutanol following the general procedure previously described. Approximately 1070 grams of isobutanol were reacted with 790 grams of $P_2S_5$ at about 70 to 80° F. for about 4 hours. The byproduct $H_2S$ was vented. The solution was cooled and filtered to remove unreacted $P_2S_5$. Approximately 3655 grams of the aforementioned sulfurized olefin prepared in accordance with Example 1 was reacted with 915 grams of O,O-diisobutylphosphorodithioic acid at 90°–100° C. for about 10 hours with a slow $H_2S$ sparge to form an adduct. The crude reaction product was sparged with $N_2$ to remove any excess $H_2S$.

The product was analyzed, with the following results:

| | Found |
| --- | --- |
| Phosphorus, Wt. % | 2.3 |
| Sulfur, Wt. % | 35.8 |
| Carbon, Wt. % | 42.9 |
| Hydrogen, Wt. % | 6.9 |

EXAMPLE 4

Adduct of Mixed O-2-Propyl O-2-ethylhexylphosphorodithioic Acid

O-2-propyl O-2-ethylhexylphosphorodithioic acid was made following the procedure of Example 3 by the reaction of an equal molar mixture of 2-propanol and 2-ethylhexanol with phosphorus pentasulfide. Approximately 3,200 grams of the sulfurized olefin prepared in accordance with Example 1 was then reacted with 935 grams of the O-2-propyl O-2-ethylhexylphosphorodithioic acid to form a phosphorus- and sulfur-containing adduct by reaction at 85°–100° C. for about 5 hours with agitation and a slow $H_2S$ sparge. The crude reaction product was sparged for one more hour with $N_2$ to remove any excess $H_2S$.

| Product Analysis: | |
| --- | --- |
| Phosphorus, Wt. % | 2.17 |
| Sulfur, Wt. % | 35.3 |
| Carbon, Wt. % | 43.2 |
| Hydrogen, Wt. % | 6.9 |

EXAMPLE 5

Adduct of Mixed O-2-Propyl O-2-ethylhexylphosphorodithioic Acid

O-2-propyl O-2-ethylhexylphosphorodithioic acid was made following the procedure of Example 4 by the reaction of an equal molar mixture of 2-propanol and 2-ethylhexanol with phosphorus pentasulfide. Approximately 1200 grams of the sulfurized olefin prepared in accordance with Example 2 was then reacted with 375 grams of the O-2-propyl O-2-ethylhexylphosphorodithioic acid to form an adduct by reaction at 90°–100° C. for about 13 hours with agitation and a slow $H_2S$ sparge. The crude reaction product was sparged for 2 more hours with $N_2$ to remove any residual $H_2S$.

| Product Analysis: | |
| --- | --- |
| Phosphorus, Wt. % | 2.0 |
| Sulfur, Wt. % | 35.1 |
| Carbon, Wt. % | 49.9 |
| Hydrogen, Wt. % | 8.2 |

EXAMPLE 6

Adduct of O,O-Di-4-methyl-2-pentylphosphorodithioic Acid

O,O-Di-4-methyl-2-pentylphosphorodithioic acid was made following the procedure of Example 3 by the reaction of 4-methyl-2-pentanol with phosphorus pentasulfide. Approximately 3599 grams of the sulfurized olefin prepared in accordance with Example 1 was then reacted with 1060 grams of the O,O-di-4-methyl-2-pentylphosphorodithioic acid to form an adduct by reaction at 85°–95° C. for about 9 hours with agitation and a slow $H_2S$ sparge. The crude reaction product was sparged for 1½ more hours at 85° C. to remove any excess $H_2S$.

| Product Analysis: | |
| --- | --- |
| Phosphorus, Wt. % | 1.75 |
| Sulfur, Wt. % | 33.4 |
| Carbon, Wt. % | 43.1 |
| Hydrogen, Wt. % | 7.1 |

EXAMPLE 7

Zinc Oxide Treated O,O-Diisobutylphosphorodithioic Acid-Sulfurized Olefin Adduct Approximately 350 grams of O,O-diisobutylphosphorodithioic acid-sulfurized olefin adduct prepared in accordance with Example 3 was reacted with 24 grams of zinc oxide at about 90° C. with agitation for 4 hours in the presence of about 70 ml. benzene as solvent. The benzene solvent was removed by heating to 90° C. under reduced pressure and the excess zinc oxide was removed by filtration over diatomaceous earth. The product was a clear orange viscous liquid.

Product Analysis:

| | |
|---|---|
| Zinc, Wt. % | 0.56 |
| Phosphorus, Wt. % | 2.3 |
| Sulfur, Wt. % | 34.0 |

EXAMPLE 8

Zinc Oxide Treated O,O-Diisobutylphosphorodithioic Acid-Sulfurized Olefin Adduct Approximately 165 grams of O,O-diisobutylphosphorodithioic acid-sulfurized olefin adduct prepared in accordance with Example 3 was reacted with 4 grams of zinc oxide at about 90° C. for 4 hours with agitation in the presence of 50 ml. benzene as solvent. The benzene solvent was removed by heating to 90° C. under reduced pressure and the excess zinc oxide was removed by filtration over diatomaceous earth. The product was a clear orange liquid.

Product Analysis:

| | |
|---|---|
| Zinc, Wt. % | 0.49 |
| Phosphorus, Wt. % | 2.3 |
| Sulfur, Wt. % | 35.3 |

EXAMPLE 9

Zinc Oxide Treated O,O-Di-4-methyl-2-pentylphosphorodithioic Acid-Sulfurized Olefin Adduct Approximately 3800 grams of O,O-di-4-methyl-2-pentylphosphorodithioic acid-sulfurized olefin adduct prepared in accordance with Example 6 was reacted with 50 grams of zinc oxide at about 90° C. with agitation for 4 hours in the presence of about 500 ml. 2-propanol used as a solvent. The 2-propanol solvent was removed by heating to 90° C. under reduced pressure and the excess zinc oxide was removed by filtration over diatomaceous earth. The product was a clear orange liquid.

Product Analysis:

| | |
|---|---|
| Zinc, Wt. % | 0.41 |
| Phosphorus, Wt. % | 1.5 |
| Sulfur, Wt. % | 34.5 |
| Carbon, Wt. % | 47.4 |
| Hydrogen, Wt. % | 7.7 |

EXAMPLE 10

Zinc Oxide Treated O-2-Propyl O-2-ethylhexylphosphorodithioic Acid-Sulfurized Olefin Adduct Approximately 3485 grams of O-2-propyl O-2-ethylhexylphosphorodithioic acid-sulfurized olefin adduct prepared in accordance with Example 4 was reacted with 45 grams of zinc oxide at about 85°–90° C. with agitation for 4 hours in the presence of about 400 ml. 2-propanol used as a solvent. The 2-propanol solvent was removed by heating to 90° C. under reduced pressure and the excess zinc oxide was removed by filtration over diatomaceous earth. The product was a clear orange liquid.

Product Analysis:

| | |
|---|---|
| Zinc, Wt. % | 0.63 |
| Phosphorus, Wt. % | 2.3 |
| Sulfur, Wt. % | 33.8 |
| Carbon, Wt. % | 47.7 |
| Hydrogen, Wt. % | 7.7 |

EXAMPLE 11

Magnesium Oxide Treated O-2-Propyl O-2-ethylhexylphosphorodithioic Acid-Sulfurized Olefin Adduct Approximately 123 grams of O-2-propyl O-2-ethylhexylphosphorodithioic acid-sulfurized olefin adduct prepared in accordance with Example 4 was reacted with 6 grams of magnesium oxide at about 90° C. with agitation for 4½ hours in the presence of about 25 ml. 2-propanol as solvent. The 2-propanol solvent was removed by heating to 90° C. under reduced pressure and the excess magnesium oxide was removed by filtration over diatomaceous earth.

Product Analysis:

| | |
|---|---|
| Magnesium Wt. % | 0.13 |
| Phosphorus, Wt. % | 1.9 |
| Sulfur, Wt. % | 36.0 |
| Carbon, Wt. % | 49.3 |
| Hydrogen, Wt. % | 8.0 |

EXAMPLE 12

Calcium Oxide Treated O-2-Propyl O-2-ethylhexylphosphorodithioic Acid-Sulfurized Olefin Adduct Approximately 83 grams of O-2-propyl O-2-ethylhexylphosphorodithioic acid-sulfurized olefin adduct prepared in accordance with Example 4 was reacted with 4 grams of calcium oxide at 85°–90° C. with agitation for 4½ hours in the presence of 25 ml. 2-propanol as solvent. The 2-propanol solvent was removed by heating to 90° C. under reduced pressure and the excess calcium oxide was removed by filtration over diatomaceous earth. The product was a clear orange liquid.

Product Analysis:

| | |
|---|---|
| Calcium, Wt. % | 0.16 |
| Phosphorus, Wt. % | 1.9 |
| Sulfur, Wt. % | 36.4 |
| Carbon, Wt. % | 51.0 |
| Hydrogen, Wt. % | 7.9 |

EXAMPLE 13

Barium Oxide Treated O-2-Propyl O-2-ethylhexylphosphorodithioic Acid-Sulfurized Olefin Adduct Approximately 90 grams of O-2-propyl O-2-ethylhexylphosphorodithioic acid-sulfurised olefin prepared in accordance with Example 4 was reacted with 12 grams of barium oxide at about 85°–90° C. with agitation for 6 hours in the presence of 25 ml. 2-propanol as solvent. The 2-propanol solvent was removed by heating to 90° C. under reduced pressure and the excess barium oxide was removed by filtration over diatomaceous earth. The product was a clear liquid.

| Product Analysis: | |
|---|---|
| Barium, Wt. % | 0.95 |
| Phosphorus, Wt. % | 1.9 |
| Sulfur, Wt. % | 34.0 |
| Carbon, Wt. % | 51.3 |
| Hydrogen, Wt. % | 7.8 |

EXAMPLE 14

Cobaltous Acetate Treated O-2-Propyl O-2-ethylhexylphosphorodithioic Acid-Sulfurized Olefin Adduct Approximately 80 grams of O-2-propyl O-2-ethylhexylphosphorodithioic acid-sulfurized olefin adduct prepared in accordance with Example 4 was reacted with 6 grams of cobaltous acetate tetrahydrate at about 75°–85° C. with agitation for 6 hours in the presence of 25 ml. 2-propanol as solvent. The 2-propanol solvent was removed by heating to 90° C. under reduced pressure and the excess cobaltous acetate was removed by filtration over diatomaceous earth.

| Product Analysis: | |
|---|---|
| Cobalt, Wt. % | 0.26 |
| Phosphorus, Wt. % | 1.9 |
| Sulfur, Wt. % | 35.9 |
| Carbon, Wt. % | 52.3 |
| Hydrogen, Wt. % | 7.9 |

EXAMPLE 15

Cupric Acetate Treated O-2-Propyl O-2-ethylhexylphosphorodithioic Acid-Sulfurized Olefin Adduct Approximately 67 grams of O-2-propyl O-2-ethylhexylphosphorodithioic acid-sulfurized olefin adduct prepared in accordance with Example 5 was reacted with 4½ grams of cupric acetate monohydrate at about 75°–85° C. with agitation for 5½ hours in the presence of 25 ml. 2-propanol used as a solvent. The 2-propanol solvent was removed by heating to 90° C. under reduced pressure and the excess cobaltous acetate was removed by filtration over diatomaceous earth.

| Product Analysis: | |
|---|---|
| Copper, Wt. % | 0.45 |
| Phosphorus, Wt. % | 2.0 |
| Sulfur, Wt. % | 36.6 |
| Carbon, Wt. % | 50.4 |
| Hydrogen, Wt. % | 7.6 |

EXAMPLE 16

Molybdenum Oxide Treated O-2-Propyl O-2-ethylhexylphosphorodithioic Acid-Sulfurized Olefin Adduct Approximately 95 grams of O-2-propyl O-2-ethylhexylphosphorodithioic acid-sulfurized olefin adduct prepared in accordance with Example 4 was reacted with 9 grams of molybdenum trioxide at about 80°–90° C. with agitation for 4 hours in the presence of 25 ml. water, 40 ml. 2-propanol and 25 ml. isobutanol solvents. The solvents were removed by heating to about 115° C. under reduced pressure and the excess molybdenum trioxide was removed by filtration over diatomaceous earth. The product was a clear blue-black liquid.

| Product Analysis: | |
|---|---|
| Molybdenum Wt. % | 0.6 |
| Phosphorus, Wt. % | 2.29 |
| Sulfur, Wt. % | 38.6 |
| Carbon, Wt. % | 44.9 |
| Hydrogen, Wt. % | 7.4 |

EVALUATION OF THE PRODUCTS

Representative samples of the metal salt adducts were tested in as follows:

Standard 4-Ball Wear Test

Table 1 summarizes the results obtained under the conditions shown.

TABLE 1

| 4 BALL WEAR SCAR DIAMETER (MM) ½" BALLS, 52100 STEEL, 60 KG LOAD, 30 MINUTES | | | | | | |
|---|---|---|---|---|---|---|
| | Conc., Wt. % | Temp., °F. | Speed (RPM) | | | |
| | | | 500 | 1000 | 1500 | 2000 |
| Base Stock* | 100 | Room | 0.50 | 0.60 | 0.88 | 2.34 |
| | | 200 | 0.60 | 1.06 | 1.86 | 2.23 |
| | | 390 | 1.00 | 1.31 | 2.06 | — |
| Example 7 | 1.0 | Room | 0.50 | 0.53 | 0.85 | 1.25 |
| | | 200 | 0.90 | 0.80 | 0.80 | 1.25 |
| | | 390 | 1.40 | 1.65 | 1.75 | 1.80 |
| Example 8 | 1.0 | Room | 0.60 | 0.53 | 0.85 | 1.18 |
| | | 200 | 0.90 | 0.73 | 0.70 | 1.40 |
| | | 390 | 1.50 | 1.15 | 2.00 | 1.66 |

*The base stock was an 80/20 mixture of bright stock mineral oil and 200" solvent paraffinic neutral lubricating oils.

Copper Corrosion

This test was run at 210° F. for 6 hours in accordance with ASTM No. D130-9. The base oil was a 200-second solvent paraffinic netural mineral oil. The lower the value shown in Table 2, the better the additive performance.

Representative samples of the above prepared adducts were also tested for copper corrosivity using ASTM No. D130-9 at 210° F. for 6 hours and also for antioxidant properties with a catalytic oxidation test at 325° C. for 40 hours as described below.

Catalytic Oxidation Test

A sample of the base lubricant was placed in an oven at a desired temperature. Present in the same were the following metals either known to catalyze organic oxidation or commonly used material of construction.

a. 15.6 sq. in. of sand-blasted iron wire,
b. 0.78 sq. in. of polished copper wire,
c. 0.87 sq. in. of polished aluminum wire, and
d. 0.167 sq. in of polished lead surface.

Dry air was passed through the sample at a rate of about 5 liters per hour.

The results of this test are summarized in Table 3.

TABLE 2

| Copper Corrosion Test - ASTM No. D130-9 (6 hrs. at 210° F.) Base Oil - 200" Solvent Parraffinic Neutral | | |
|---|---|---|
| Example No. | 1% Additive In Base Oil | 3% Additive In Base Oil* |
| Example 3 | 3B | 3B |

TABLE 2-continued

Copper Corrosion Test -
ASTM No. D130-9 (6 hrs. at 210° F.)
Base Oil - 200" Solvent Parraffinic Neutral

| Example No. | 1% Additive In Base Oil | 3% Additive In Base Oil* |
|---|---|---|
| Example 4 | 3B | 4A |
| Example 5 | — | 3B |
| Example 6 | — | 3B |
| Example 7 | 1A | 1A |
| Example 8 | 1A | 1A |
| Example 9 | 1B | 1B |
| Example 10 | 1A | 1A |
| Example 11 | 3A | 3B |
| Example 12 | — | 3B |
| Example 13 | — | 3B |
| Example 14 | 3A | 3B |
| Example 15 | — | 3B |
| Example 16 | 2B | 3B |

*The lower the rating, the better the additive performance.

TABLE 3

CATALYTIC OXIDATION TEST (325° F., 40 hrs.)

| | Concentration, Wt. % | Lead Loss, Mg. | Percent Increase in Viscosity of Oxidized Oil, KV at 210° F. | Neutralization Number, NN |
|---|---|---|---|---|
| Base Oil*, No Additive | | 0.4 | 27 | 2.21 |
| Example 7 | 1 | 0.0 | 12 | 1.35 |
| Example 8 | 1 | 0.2 | 9 | 0.97 |
| Example 9 | 1 | 0.0 | 8 | 1.41 |
| Example 10 | 1 | 0.0 | 10 | 0.98 |
| Example 11 | 1 | 0.5 | 7 | 1.15 |
| Example 12 | 1 | 0.4 | 9 | 1.19 |
| Example 13 | 1 | 0.0 | 16 | 1.24 |
| Example 14 | 1 | 0.0 | 17 | 1.05 |
| Example 15 | 1 | 0.0 | 17 | 1.10 |
| Example 16 | 1 | 0.0 | 4 | 0.53 |

*200" solvent paraffinic neutral mineral oil.

The data shown in the tables clearly establish that the novel compounds of this invention provide good antioxidant and antiwear properties to lubricants while maintaining or improving good copper strip corrosivity.

While the process of the present invention has been described in detail in conjunction with the treatment of a limited number of compounds under similar conditions for the purposes of valid comparisons and of fully illustrating the invention, it will be readily apparent to those of ordinary skill in the art that numerous modifications and variations are within the purview of this invention.

What is claimed is:

1. An organothiophosphorus compound comprising a metal salt of the reaction product of (1) a phosphorodithioic acid having the general formula:

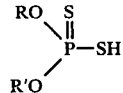

wherein R and R' are hydrocarbyl and are the same or different with each having up to about 30 carbon atoms and (2) a sulfurized olefin having from about 2 to about 8 carbon atoms and sufficient reactive olefinic sites to react with said acid, thereby incorporating into the resultant organothiophosphorus compound from about 0.1 to about 10 wt. % of phosphorus.

2. The compound of claim 1 wherein R and R' are diisobutyl.

3. The compound of claim 1 wherein R is propyl and R' is 2-ethylhexyl.

4. The compound of claim 1 wherein R and R' are 4-methyl-2-pentyl.

5. The compound of claim 1 wherein the metal of the metal salt is selected from Groups IB, IIA, IIB, IVA, VIB or VIII of the Periodic Table.

6. The compound of claim 5 wherein the metal is zinc.

7. The compound of claim 5 wherein the metal is magnesium.

8. The compound of claim 5 wherein the metal is calcium.

9. The compound of claim 5 wherein the metal is barium.

10. The compound of claim 5 wherein the metal is cobalt.

11. The compound of claim 5 wherein the metal is copper.

12. The compound of claim 5 wherein the metal is molybdenum.

13. A lubricant composition comprising a major amount of a lubricant and from about 0.01 to about 10% of an organothiophosphorus compound comprising a metal salt of the reaction product of (1) a phosphorodithioic acid having the general formula:

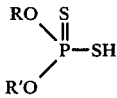

wherein R and R' are hydrocarbyl and are the same or different with each having up to about 30 carbon atoms and (2) a sulfurized olefin having from about 2 to about 8 carbon atoms and sufficient reactive olefinic sites to react with said acid, thereby incorporating into the resultant organothiophosphorus compound from about 0.1 to about 10 wt. % of phosphorus.

14. The composition of claim 13 wherein R and R' are diisobutyl.

15. The composition of claim 13 wherein R is propyl and R' is 2-ethylhexyl.

16. The composition of claim 13 wherein R and R' are 4-methyl-2-pentyl.

17. The composition of claim 13 wherein the metal of the metal salt is selected from Groups IB, IIA, IIB, IVA, VIB or VIII of the Periodic Table.

18. The composition of claim 17 wherein the metal is zinc.

19. The composition of claim 17 wherein the metal is magnesium.

20. The composition of claim 17 wherein the metal is calcium.

21. The composition of claim 17 wherein the metal is barium.

22. The composition of claim 17 wherein the metal is cobalt.

23. The composition of claim 17 wherein the metal is copper.

24. The composition of claim 17 wherein the metal is molybdenum.